(12) United States Patent
Miyamoto et al.

(10) Patent No.: US 7,131,171 B2
(45) Date of Patent: Nov. 7, 2006

(54) METHOD FOR RESTORING BULKINESS OF NONWOVEN FABRIC

(75) Inventors: Takanobu Miyamoto, Tochigi (JP); Wataru Saka, Tochigi (JP); Yasuhiro Komori, Tochigi (JP); Koji Asano, Tochigi (JP); Manabu Kaneta, Tochigi (JP)

(73) Assignee: Kao Corporation, Tokyo (JP)

( * ) Notice: Subject to any disclaimer, the term of this patent is extended or adjusted under 35 U.S.C. 154(b) by 315 days.

(21) Appl. No.: 10/668,201

(22) Filed: Sep. 24, 2003

(65) Prior Publication Data

US 2004/0111848 A1 Jun. 17, 2004

(30) Foreign Application Priority Data

| | | |
|---|---|---|
| Sep. 25, 2002 | (JP) | ............................. 2002-280081 |
| Jun. 24, 2003 | (JP) | ............................. 2003-180240 |

(51) Int. Cl.
*B65H 71/00* (2006.01)

(52) U.S. Cl. ............................. 28/166; 28/122; 28/112

(58) Field of Classification Search ................. 28/100, 28/104, 116, 122, 156, 112, 115
See application file for complete search history.

(56) References Cited

U.S. PATENT DOCUMENTS 3,406,033 A * 10/1968 Reitz ........................... 427/173
4,601,937 A * 7/1986 Latussek ..................... 428/132
4,857,065 A * 8/1989 Seal ............................ 604/368
5,143,779 A   9/1992 Newkirk et al.
5,368,925 A * 11/1994 Hosokawa et al. ......... 442/359

FOREIGN PATENT DOCUMENTS

| | | |
|---|---|---|
| EP | 0404032 A1 | 12/1990 |
| EP | 0538047 A1 | 4/1993 |
| JP | 3-220355 A | 9/1991 |
| JP | 4-142922 A | 5/1992 |
| JP | 6-158499 A | 6/1994 |
| JP | 2000-336569 A | 12/2000 |
| JP | 2002-187228 A | 7/2002 |
| WO | WO-97/48846 A1 | 12/1997 |

* cited by examiner

*Primary Examiner*—Danny Worrell
(74) *Attorney, Agent, or Firm*—Birch, Stewart, Kolasch & Birch, LLP

(57) ABSTRACT

A method for restoring bulkiness of nonwoven fabric which contains crimped thermoplastic fiber and is in a roll form is disclosed. The method comprises unwinding the nonwoven fabric from the stock roll, and blowing hot air to the unwound nonwoven fabric by a through-air technique to make the nonwoven fabric increase in bulkiness. The hot air is heated at a temperature lower than the melting point of the thermoplastic fiber and not lower than a temperature lower than that melting point by about 50° C., and is blown for about 0.05 to 3 seconds.

17 Claims, 5 Drawing Sheets

METHOD FOR RESTORING BULKINESS OF NONWOVEN FABRIC

FIELD OF THE INVENTION

The present invention relates to a method of restoring bulkiness of nonwoven fabric whose bulkiness has been reduced under winding pressure. The present invention also relates to a method of producing an absorbent article having a nonwoven fabric wherein the bulkiness has been restored by the method above.

BACKGROUND OF THE INVENTION

Nonwoven fabric manufactured by a prescribed process is often wound and stored in a roll form and then transported to another line, where it is unwound and fabricated into a desired product. The nonwoven fabric in roll form tends to lose its bulkiness under the winding pressure. The greater the bulkiness is, the more conspicuous this tendency becomes.

JP-A-3-220355 discloses a nonwoven fabric capable of restoring bulkiness by 5 or more fold expansion, which has constituent fibers thereof bound with a fiber binding adhesive and is restrained in a state compressed by a temporary adhesive having a melting point lower than the melting point of each of the constituent fibers and the fiber binding adhesive. The nonwoven fabric restores its bulkiness upon being heated at a temperature equal to or higher than the melting point of the temporary adhesive and lower than the melting point of each of the constituent fibers and the fiber binding adhesive. JP-A-4-142922 discloses a material capable of increasing bulkiness, which contains a compressed nonwoven fabric capable of increasing in thickness upon being heated and a sheet material, wherein the compressed nonwoven fabric and the sheet material are joined with an adhesive. The compressed nonwoven fabric is a bulky nonwoven fabric having been compressed into a thinner fabric and held in the compressed state by thermally fusible fibers or low-melting resin particles. On being heated by dry heat or wet heat, the bonds by the thermally fusible fibers or low-melting resin particles in the compressed nonwoven fabric loosen to allow the constituent fibers to restore its bulkiness by its own restoring force. The above-described nonwoven fabrics are intentionally made to reduce its bulkiness by using a temporary adhesive, thermally fusible fibers or low-melting resin particles in order to facilitate sewing or like fabrication steps of the nonwoven fabric. Hence, the techniques disclosed have no direct relation to the reduction in bulkiness due to winding pressure.

JP-A-6-158499 proposes a process of producing nonwoven fabric, in which a fiber aggregate containing thermally bonding fibers having a low-melting component and a high-melting component is subjected to heat treatment followed by a cooling treatment to bond the thermally bonding fibers. In this process, the fiber aggregate is heated with hot air at or above the melting point of the low-melting component blown at a velocity of 0.2 to 5 m/sec for 0.1 to 300 seconds and, immediately thereafter, cooled with a low temperature gas (−30 to 45° C.) blown at such a low velocity as to apply no flow pressure, i.e., a velocity of 0.1 to 1 m/sec for 0.1 second or longer, thereby solidifying the low-melting component. This technique is to address the problem of bulkiness reduction caused by blowing low-temperature gas in the nonwoven fabric manufacturing and therefore has no direct relation to the reduction of bulkiness due to winding pressure.

SUMMARY OF THE INVENTION

The present invention provides a method for restoring bulkiness of nonwoven fabric which contains crimped thermoplastic fiber and is in a roll form, which steps include:
unwinding the nonwoven fabric from a stock roll and
blowing hot air to the unwound nonwoven fabric by a through-air technique to make the nonwoven fabric increase in bulkiness, the hot air being heated at a temperature lower than the melting point of the thermoplastic fiber and not lower than a temperature lower than that melting point by about 50° C., and being blown for about 0.05 to 3 seconds.

The present invention also provides a process of producing a nonwoven fabric which steps include:
preparing a nonwoven fabric containing crimped thermoplastic fiber by a prescribed process and winding the nonwoven fabric into a stock roll,
unwinding the nonwoven fabric from the stock roll, and
blowing hot air to the unwound nonwoven fabric by a through-air technique to make the nonwoven fabric increase in bulkiness, the hot air being heated at a temperature lower than the melting point of the thermoplastic fiber and not lower than a temperature lower than the melting point by about 50° C., and being blown for about 0.05 to 3 seconds.

The present invention also provides a process of producing an absorbent article having a liquid permeable topsheet, a liquid impermeable backsheet, and a liquid retentive absorbent member interposed between the topsheet and the backsheet,
the topsheet being made of a nonwoven fabric which contains crimped thermoplastic fiber and has been wound into a stock roll before being fabricated into the absorbent article,
which process includes the steps of:
unwinding the nonwoven fabric from the stock roll and
blowing hot air to the unwound nonwoven fabric by a through-air technique to make the nonwoven fabric increase in bulkiness, the hot air being heated at a temperature lower than the melting point of the thermoplastic fiber and not lower than a temperature lower than that melting point by about 50° C., and being blown for about 0.05 to 3 seconds.

The present invention also provides a process of producing an absorbent article comprising a liquid permeable topsheet, a liquid impermeable backsheet, a liquid retentive absorbent member interposed between the topsheet and the backsheet, and an intermediate sheet interposed between the topsheet and the absorbent member,
at least one of the topsheet and the intermediate sheet being made of nonwoven fabric which contains crimped thermoplastic fiber and has been wound into a stock roll before being fabricated into the absorbent article,
which process includes the steps of:
unwinding the nonwoven fabric from the stock roll and
blowing hot air to the unwound nonwoven fabric by a through-air technique to make the nonwoven fabric increase in bulkiness, the hot air being heated at a temperature lower than the melting point of the thermoplastic fiber and not lower than a temperature lower than that melting point by about 50° C., and being blown for about 0.05 to 3 seconds.

The present invention also provides a nonwoven fabric produced by unwinding a nonwoven fabric containing crimped thermoplastic fiber from a stock roll and blowing hot air to the unwound nonwoven fabric by a through-air technique to make the nonwoven fabric increase in bulkiness, the hot air being heated at a temperature lower than the melting point of the thermoplastic fiber and not lower than a temperature lower than that melting point by about 50° C., and being blown for about 0.05 to 3 seconds.

The present invention also provides a method for restoring bulkiness of nonwoven fabric which contains crimped thermoplastic fiber and is in a roll form while the nonwoven fabric is being unwound and transferred, the method including the steps of:

heating the unwound nonwoven fabric while the nonwoven fabric is being transferred at a heating temperature lower than the melting point of the thermoplastic fiber and not lower than a temperature lower than the melting point by about 50° C., and transferring the heated nonwoven fabric at a speed lower than the transfer speed during heating thereby making the nonwoven fabric increase in bulkiness.

The present invention also provides a process of producing an absorbent article having a liquid permeable topsheet, a liquid impermeable backsheet, and a liquid retentive absorbent member interposed between the topsheet and the backsheet, the topsheet being made of a nonwoven fabric which contains crimped thermoplastic fiber and has been wound into a stock roll before being fabricated into the absorbent article, which process includes the steps of:

unwinding and transferring the nonwoven fabric from a stock roll, heating the unwound nonwoven fabric while the nonwoven fabric is being transferred at a temperature lower than the melting point of the thermoplastic fiber and not lower than a temperature lower than the melting point by about 50° C., and transferring the heated nonwoven fabric at a speed lower than the transfer speed during heating, thereby making the nonwoven fabric increase in bulkiness.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings, in which like designations are used to designate substantially identical elements, and in which:

DETAILED DESCRIPTION OF THE INVENTION

All publications cited herein are hereby incorporated by reference.

The present invention relates to a method for easily restoring bulkiness of nonwoven fabric that has been reduced in thickness due to winding pressure. The present invention also relates to a method of producing an absorbent article which gives little discomfort due to backflow of absorbed liquid or due to the remaining liquid on the topsheet and which allows even a high viscosity liquid to reach the absorbent member thereof rapidly. The present invention will be described based on its preferred embodiments with reference to the accompanying drawings.

Figure 1:
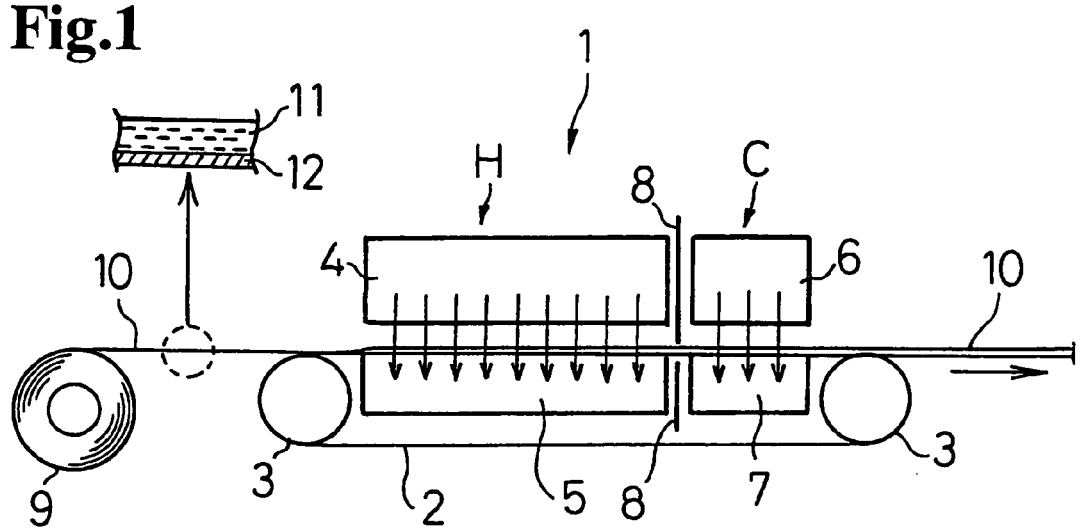
FIG. 1 schematically illustrates an apparatus which can be used to carry out a method of the present invention.

FIG. 1 schematically illustrates a bulkiness restoring apparatus which can be used to carry out one embodiment of the present invention. The apparatus 1 shown in FIG. 1 includes a conveyer belt 2 made of a wire mesh, a heating zone H, and a cooling zone C. The conveyer belt 2, which is endless, runs in a direction around supporting axes 3. The heating zone H is positioned upstream while the cooling zone C is positioned downstream with respect to the running direction of the upper run of the conveyer belt 2. The conveyer belt 2 is made of a metal or a resin, such as polyethylene terephthalate. A belt made of a resin such as polyethylene terephthalate is preferred from the standpoint of heat dissipation efficiency.

A first blower 4 is placed above the conveyer belt 2 to face the upper run of the conveyer belt 2. The first blower 4 blows hot air heated at a prescribed temperature toward the conveyer belt 2. On the opposite side of the upper run of the conveyer belt 2 is placed a first suction box 5 which sucks the hot air blown from the first blower 4. The first blower 4 and the first suction box 5 constitute the heating zone H. The hot air sucked by the first suction box 5 is sent to the first blower 4 through a duct (not shown). That is, hot air is circulated between the first blower 4 and the first suction box 5.

A second blower 6 is placed in the immediate downstream of the first blower 4 to face the upper run of the conveyer belt 2. The second blower blows cool air at a prescribed temperature against the conveyer belt 2. On the opposite side of the upper run of the conveyer belt 2 is placed a second suction box 7 which sucks the cool air blown from the second blower 6. The second blower 6 and the second suction box 7 constitute the cooling zone C. The cool air sucked by the second suction box 7 is driven out of the apparatus through a duct (not shown). That is, cool air is not circulated between the second blower 6 and the second suction box 7. If circulated, the cool air increases in temperature to reduce the cooling efficiency.

A partition 8 is provided between the first blower 4 and the second blower 6 and between the first suction box 5 and the second suction box 7. The partitions 8 prevent hot air and cool air from being mixed together.

Figure 2A:
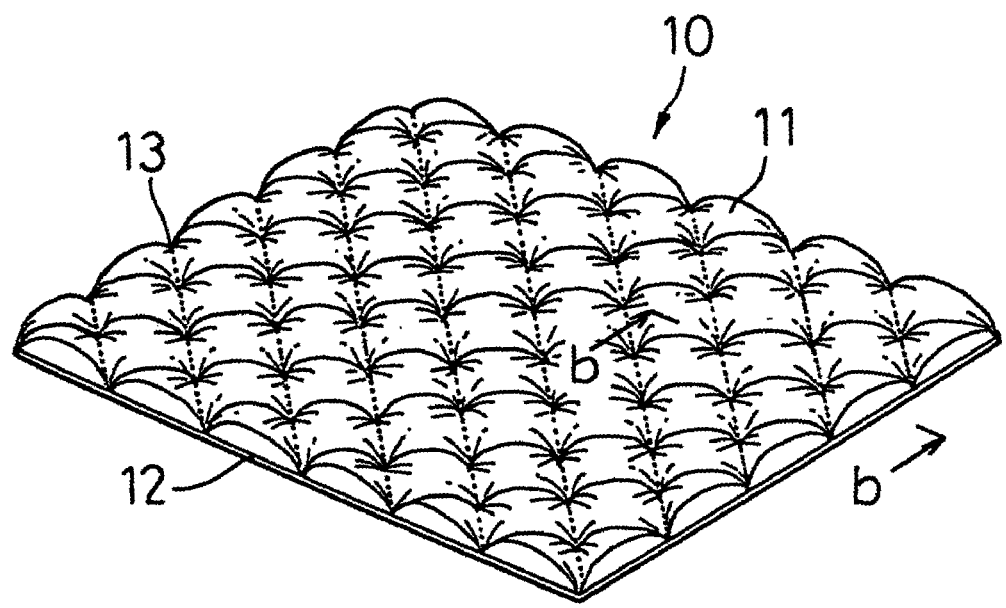
FIG. 2(a) is a perspective of a nonwoven fabric which can be treated by a method of the present invention.
Figure 2B:
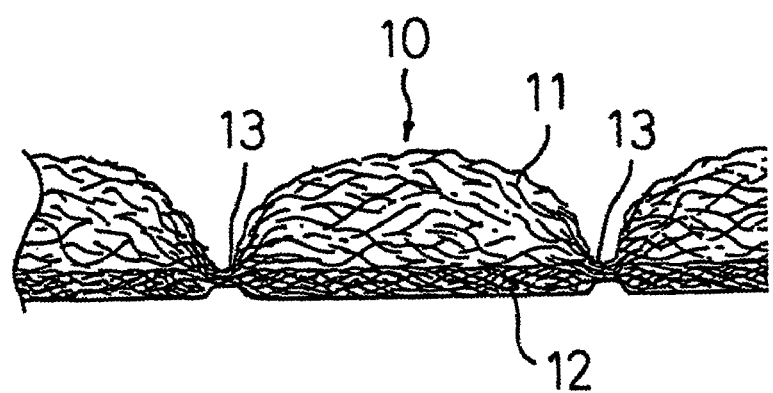
FIG. 2(b) is a cross-section of the nonwoven fabric of FIG. 2(a), taken along line b—b.

The first embodiment of the method using the apparatus 1 is carried out as follows. The nonwoven fabric 10 that is to be treated in the embodiment has a three-dimensional bulky structure as depicted in FIGS. 2(a) and 2(b). It has a multilayer structure composed of two layers, i.e., a first layer 11 and a second layer 12 adjacent thereto. The first layer 11 and the second layer 12 are joined together in parts indicated by a large number of joints 13. The joints 13 form a diamond lattice pattern as a whole. The individual joints 13 are densified parts having a smaller thickness and a higher density than other parts of the nonwoven fabric 10. The joint has for example a rectangular, linear or star shape. The joint 13 shown in FIGS. 2(a) and 2(b) has a circular shape.

The nonwoven fabric 10 has a great number of parts that are each surrounded by the joints 13 arranged in a diamond shape. In each of these parts, the first layer 11 forms a dome-shaped protrusion, while the second layer 12 is almost flat. Seen as a whole, the nonwoven fabric 10 has a flat surface on the second layer 12 side and numerous protrusions on the first layer 11 side.

The first layer 11 contains crimped thermoplastic fibers (hereinafter simply referred to as "crimped fibers"). The crimped fibers include those with a two-dimensional crimp and those with a helical crimp. The first layer 11 can be made solely of crimped fibers or may comprise crimped fibers and thermally fusible fibers, such as sheath/core conjugate fibers or side-by-side conjugated fibers. Whatever fiber is used, the fiber of the first layer 11 should have substantially no heat shrinkability or, if any, should not shrink at temperatures below the heat shrinkage temperature of the heat shrinkable fiber (hereinafter described) used in the second layer 12. The crimped fiber preferably has a fineness of 1 to 11 dtex, particularly 1.5 to 7 dtex, for assuring satisfactory feel or texture and liquid permeability. On the other hand, the second layer 12 contains heat shrinkable fiber. The heat shrinkable fiber preferably has a fineness of 1 to 11 dtex, particularly 2 to 7 dtex, in view of shrinkability and liquid permeability.

The preferred process for producing the nonwoven fabric 10 and the details of the materials constituting the nonwoven fabric 10 are described in U.S. Ser. No. 2002-0,068,150-A1 which was filed by the same assignee as that of the present invention, and is incorporated herein by reference. The following is a brief description of the process. A fiber material containing self-crimping fiber is carded into a first layer web. Separately, a fiber material containing heat shrinkable fiber is carded into a second layer web. The first and second layer webs are superposed on each other and partially joined in a prescribed pattern of joints by, for example, ultrasonic embossing and/or heat embossing. Hot air is then forced to penetrate through the resulting web by a through-air method at a temperature at or above the heat shrinkage initiating temperature of the heat shrinkable fiber contained in the second layer web. As a result, the second layer web shrinks whereupon the parts of the first layer web surrounded by the joints protrude, and the intersections of the constituent fibers are melt-bonded. The thus prepared nonwoven fabric 10 is wound into a stock roll for storage.

Then, as shown in FIG. 1, the stock roll 9 from which the nonwoven fabric 10 is fed is set upstream the first blower 4. The nonwoven fabric 10 in a roll form has its thickness reduced by the winding pressure. Having a three-dimensional bulky profile as stated above, the nonwoven fabric 10 has undergone appreciable reduction in bulkiness. The nonwoven fabric 10 in such a state is allowed to restore its bulkiness while passing through the apparatus 1.

The nonwoven fabric 10 unwound from the stock roll 9 is led onto the conveyer belt 2 and carried into the heating zone H, where hot air heated to a prescribed temperature is blown from the first blower 4 toward the conveyer belt 2. In the heating zone H, hot air is blown to the nonwoven fabric 10 by a through-air technique. In other words, hot air is blown to the nonwoven fabric 10 and passes through the nonwoven fabric. The present inventors have unexpectedly found that the hot air blowing in the through-flow system makes the nonwoven fabric 10 with reduced bulkiness increase its bulkiness to restore substantially the same bulkiness as before. Reduction in bulkiness of the nonwoven fabric 10 due to winding pressure is observed remarkably in the first layer 11 containing crimped fibers. It has been ascertained that the hot air blow makes the first layer 11 restore the bulkiness to a considerable degree. This means that the bulkiness restoration of the nonwoven fabric 10 relies chiefly on bulkiness restoration of the crimped fiber contained in the first layer 11. From this viewpoint, the temperature of the hot air blown to the nonwoven fabric 10 should be lower than the melting point of the crimped thermoplastic fiber (hereinafter referred to as $MP_T$) and not lower than a temperature lower than $MP_T$ by about 50° C. If the hot air temperature is lower than about $(MP_T$-50)° C., sufficient effects of hot air blowing are not produced, resulting in a failure to restore bulkiness. If the temperature of the hot air is equal to or higher than $MP_T$, the crimped fiber may melt, also resulting in a failure to restore bulkiness. To achieve effective restoration of bulkiness of the nonwoven fabric 10, a preferred temperature of the hot air ranges from about $(MP_T$-50)° C. to $(MP_T$-3)° C., preferably from about $(MP_T$-30)° to $(MP_T$-5)° C.

According to the inventors' study, blowing hot-air over a short-time is enough to produce sufficient effects. Specifically, bulkiness of the nonwoven fabric 10 can be restored by blowing hot air for as short as about 0.05 to 3 seconds, preferably about 0.05 to 1 second, more preferably about 0.05 to 0.5 second. Such shortness of the hot air blowing time largely contributes to productivity growth and size reduction of the apparatus 1. The shortness of the hot air blowing time is considered to largely be owed to the through-air technique. It is conceivable that heat application to the nonwoven fabric 10 could be conducted in a hot air rapid drying oven or by means of a hair dryer without using a through-air technique. However, bulkiness restoration may not be achieved in such a short time except by a through-air technique.

As mentioned previously, bulkiness restoration by the heat treatment with blown hot air is remarkable in the first layer 11 containing crimped fibers. To further ensure the bulkiness restoration of the first layer 11, it is preferred that hot air be blown to the first layer 11 side of the nonwoven fabric 10, that is, the nonwoven fabric 10 be carried with its second layer 12 side in contact with the conveyer belt 31. By so doing, the first layer 11, which is not in contact with the conveyer belt 31, is allowed to expand freely under no restraint.

Taking the reduction of cost of hot air and the size of the apparatus into consideration, the velocity of the hot air is preferably from about 0.5 to 10 m/sec, more preferably from about 1 to 5 m/sec, while varying depending on the temperature and the basis weight and transfer speed of the nonwoven fabric 10.

Through the above-described operation, the bulkiness of the nonwoven fabric 10 increases to about 3 to 10 times the bulkiness before hot air blowing. The thickness of the nonwoven fabric 10 increases to about 50 to 100% before it is wound into a roll form.

If the nonwoven fabric 10 having restored its bulkiness by hot air blowing is immediately subjected to a fabrication process, such as a step involving passage through nip rolls, the present inventors have realized that some cases occur in which the nonwoven fabric 10 having once restored its bulkiness undergoes reduction in bulkiness again. In order to prevent this, the inventors have found it advantageous to blow cool air to and through the nonwoven fabric 10 immediately after the bulkiness restoration by a through-air technique. By blowing in cool air, the nonwoven fabric 10 having its bulkiness restored is cooled and locked in a bulky state so that the same is prevented from reducing in bulkiness during subsequent fabrication steps using nip rolls, etc. Accordingly, the apparatus 1 shown in FIG. 1 has the preferred cooling zone C provided in the immediate downstream of the heating zone H. The expression "blow cool air to the nonwoven fabric immediately after the bulkiness restoration" means that there is no process conducted to the nonwoven fabric 10 between the blowing of hot air and cool air, and thus does not always mean that there is some time gap between the blowing of hot and cool air.

In the cooling zone C, cool air of a prescribed temperature is blown from the second blower 6 to the upper run of the conveyer belt 2. The cool air blowing is carried out by a through-air technique. That is, the cool air blown to the nonwoven fabric 10 penetrates through the nonwoven fabric 10.

The preferred temperature of the cool air for producing a sufficient cooling effect is about 50° C. or lower, more preferably about 30° C. or lower, while varying according to the kind of the nonwoven fabric constituent fiber. While there is no particular lower limit of the temperature, room temperature (about 20 to 25° C.) is preferred from the viewpoint of energy cost and for simplification of the apparatus 1.

For sufficiently cooling the nonwoven fabric 10 having been heated to a high temperature by blowing hot air, the velocity of the cool air is preferably from about 1 to 10 m/sec, more preferably from about 1 to 5 m/sec, even more preferably from about 1 to 3 m/sec. Within that range of velocity, sufficient cooling effects are exerted without disturbing the transfer of the nonwoven fabric 10.

The present inventors have ascertained that cool air blowing for a very short time is sufficient similarly to hot air blowing. Specifically, sufficient cooling of the nonwoven fabric 10 can be accomplished by blowing cool air for as an extremely short time, preferably about 0.01 second or longer, more preferably from about 0.02 to 1 second, even more preferably from about 0.05 to 0.5 second. Although not wanting to be limited by theory, accomplishment by such a short blowing time is believed to be owed to the through-air technique.

Where the nonwoven fabric 10 contains heat shrinkable fiber as in this embodiment, the nonwoven fabric 10 shrinks on being heated in the heating zone H. Shrinkage is liable to occur especially in the width direction, i.e., the transverse direction perpendicular to the machine direction. To prevent this, it is preferred that the nonwoven fabric 10 be suppressed from shrinking in the width direction thereof so that the width of the nonwoven fabric after the cool air blowing (i.e., the width of the nonwoven fabric after coming out of the cooling zone C) may be preferably about 95% or more, more preferably about 97% or more, of the width of the nonwoven fabric before the hot air blowing (i.e., the width of the nonwoven fabric before entering the heating zone H). Widthwise shrinkage can be suppressed by, for example, pinching both lateral edges of the running nonwoven fabric 10 during heating in the heating zone H and cooling in the cooling zone C. An especially convenient method is to press the nonwoven fabric 10 onto the conveyer belt 2 by hot air and cool air blown thereto at controlled velocities so that the width of the nonwoven fabric 10 does not change while the nonwoven fabric 10 is passing through the heating zone H and the cooling zone C. The velocities of the hot air and the cool air are decided within the aforementioned respective ranges, taking into consideration the basis weight and the transfer speed of the nonwoven fabric 10.

Through the above-described operations, the nonwoven fabric 10 having had its bulkiness reduced by winding pressure restores bulkiness. The nonwoven fabric 10 with restored bulkiness is then subjected to any subsequent step of fabrication. The nonwoven fabric 10 is preferably sent to the subsequent step as is, i.e., without being wound into a roll. Various fabrication steps may follow according to the use of the nonwoven fabric 10. The steps involved in the production of absorbent articles, such as sanitary napkins and disposable diapers, will be described as a typical example of such application.

An absorbent article such as a sanitary napkin or a disposable diaper includes a liquid permeable topsheet, a liquid impermeable backsheet, and a liquid retentive absorbent member interposed between the two sheets. An absorbent article having a liquid permeable intermediate sheet arranged in between the topsheet and the absorbent member is also known. The bulky nonwoven fabric 10 having the structure shown in FIGS. 2(a) and 2(b) can be used as the topsheet or the intermediate sheet in these kinds of absorbent articles. An absorbent article having such a bulky nonwoven fabric hardly causes fluid backflow to the surface (rewetting) and absorbs liquid in a vertical direction with reduced spread of liquid in the horizontal direction owing to the bulkiness of the sheet. Furthermore, the absorbent article hardly allows liquid to remain on the surface and satisfactorily transfers even a highly viscous liquid to the absorbent member. In particular, since the nonwoven fabric 10 according to a present embodiment has a three-dimensional bulky structure as shown in FIGS. 2(a) and 2(b), it has an appealing feel and appearance after being successfully restored to its original bulkiness. In the production of such absorbent articles, the nonwoven fabric 10 is unwound from the stock roll and introduced into the apparatus 1 shown in FIG. 1 where the nonwoven fabric 10 is made to restore the bulkiness by hot air blowing followed by cool air blowing. Subsequently, the nonwoven fabric 10 is introduced into a fabrication machine (not shown) for fabricating an absorbent article which is placed in the downstream of the apparatus 1, where it is united with other elements to make an absorbent article in a conventional manner. In the fabrication machine, the nonwoven fabric 10 is often subject to processing that might reduce the bulkiness, such as pinching or nipping. Even in such cases, the nonwoven fabric 10 having once restored its bulkiness by the above-described method does not undergo so large reduction in bulkiness. Finished absorbent articles are usually compressed into compact packages. The nonwoven fabric 10 does not undergo considerable reduction in bulkiness even under such compression or in compact packages. If the absorbent article is compression packaged before completion of the cooling however, the nonwoven fabric reduces in bulkiness considerably.

Another embodiment of the present invention will next be described. In this embodiment, the nonwoven fabric having been heated by hot air blowing to restore its bulkiness is allowed to cool spontaneously. The following shows how this embodiment is applied to the above-described production of absorbent articles. A nonwoven fabric is unwound from the stock roll and made to restore its bulkiness by blowing hot air. Subsequently, the nonwoven fabric is led into a fabrication machine for producing an absorbent article and fabricated into an absorbent article. While being transferred in the fabrication machine, the nonwoven fabric is allowed to cool. Spontaneous cooling is completed before a finished product is packaged. When the nonwoven fabric is cooled down to about 20 to 30° C., cooling is generally said to be completed. In the final stage of production, the absorbent article having the cooled nonwoven fabric is compression packaged. The nonwoven fabric 10 does not undergo considerable reduction in bulkiness even in such a compression packaged state.

The present invention is not construed as being limited to the above-described embodiments. For instance, the nonwoven fabric which can be treated by the method of the invention is not limited to the one shown in FIGS. 2(a) and 2(b) and includes a single- or multi-ply nonwoven fabric containing crimped fiber and a single- or multi-ply nonwoven fabric containing crimped fiber and heat shrinkable fiber. The nonwoven fabric of FIGS. 2(a) and 2(b), which has a double layer structure composed of a layer containing crimped fiber and a layer containing heat shrinkable fiber, can be replaced with other multilayer structures having three or more layers in which one or both of the outer layers contain crimped fiber and the inner layer or layers sandwiched in between the outer layers contain heat shrinkable fiber.

While the present invention is preferably applied to those nonwoven fabrics produced by a through-air method, which have high bulkiness as desired and show a high degree of bulkiness restoration, it is applicable as well to those produced by other processes, such as spun bonded nonwoven fabrics, spun laced nonwoven fabrics, and resin bonded fabrics.

Figure 3:
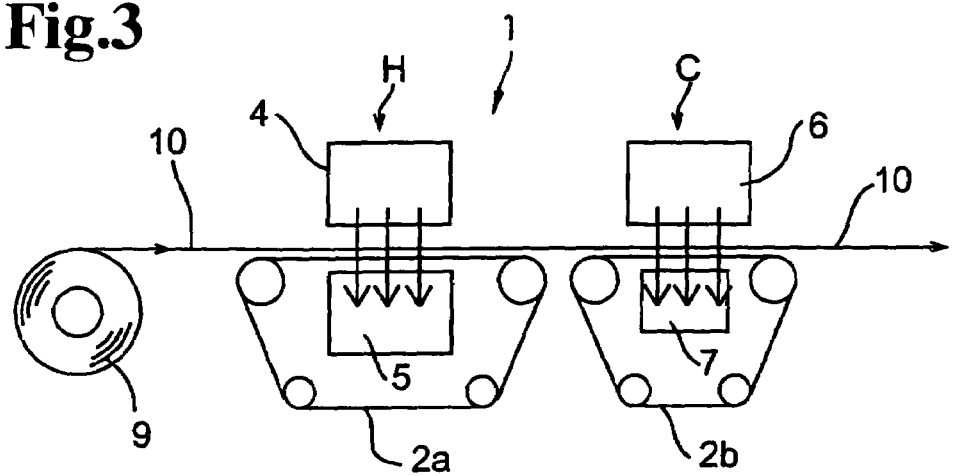
FIG. 3 schematically shows another apparatus which can be used to carry out a method of the present invention.
Figure 4:
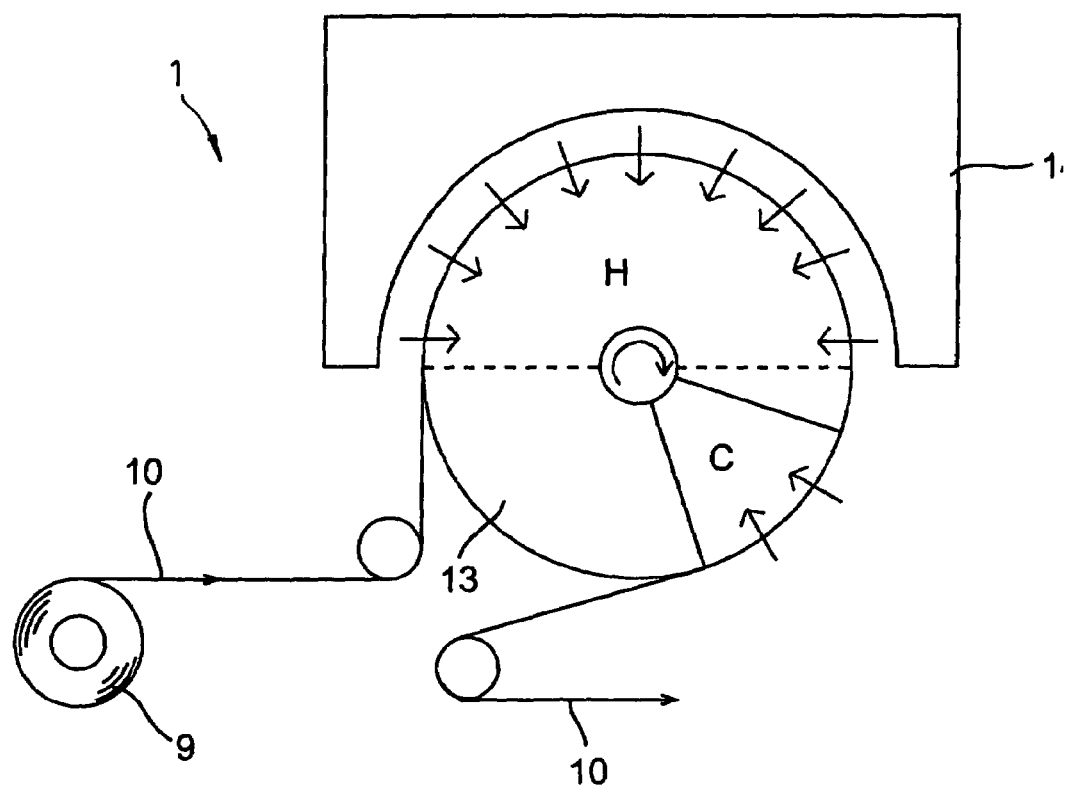
FIG. 4 schematically shows still another apparatus which can be used to carry out a method of the present invention.

The apparatus which can be used to carry out the method of the present invention includes not only the one shown in FIG. 1 but those shown in FIGS. 3 and 4. The apparatus of FIG. 3 is the same as that of FIG. 1, except that the conveyer belt 2 used in the apparatus of FIG. 1 is separated into a first conveyer belt 2a and a second conveyer belt 2b. The first conveyer belt 2a runs in the heating zone H, whereas the second conveyer belt 2b runs in the cooling zone C. In the apparatus shown in FIG. 1, since the conveyer belt 2 having been heated in the heating zone H enters the cooling zone C as heated, there is a fear that cooling efficiency cannot be raised enough. In the apparatus of FIG. 3, because the heating and the cooling zones have their own conveyers, the cooling efficiency of the nonwoven fabric 10 can be improved. Besides, the partitions used in the apparatus of FIG. 1 are no longer necessary.

The apparatus shown in FIG. 4 is of a drum type. The nonwoven fabric 10 is transferred as wrapped on a drum 13. The peripheral surface of the drum 13 is made of an air permeable material, such as punching metal or wire mesh. The drum 13 has a heating zone H and a cooling zone C. The heating zone H is upstream, and the cooling zone C is downstream, with respect to the rotating direction of the drum 13. The heating zone H occupies about ½ the peripheral surface area of the drum, while the cooling zone occupies about ⅛. The upper part of the drum 13 is covered with a hood 14, from which hot air is blown toward the drum 13 and sucked into the drum 13 through the nonwoven fabric 10. Accordingly, the part of the drum 13 covered with the hood 14 serves as the heating zone H. In the cooling zone C, open air is sucked into the drum 13 through the nonwoven fabric 10. The configuration of FIG. 4 is advantageous over those of FIGS. 1 and 3 for size reduction of the apparatus.

Next, other embodiments of the present invention will be described by way of FIGS. 5 and 6 with reference to differences from the foregoing embodiments. The explanation of the foregoing embodiments applies appropriately to those particulars of embodiments shown in FIGS. 5 and 6 that are not described here. The elements shown in FIGS. 5 and 6 that are common to FIGS. 1 to 4 are given the same reference numerals.

Figure 5:
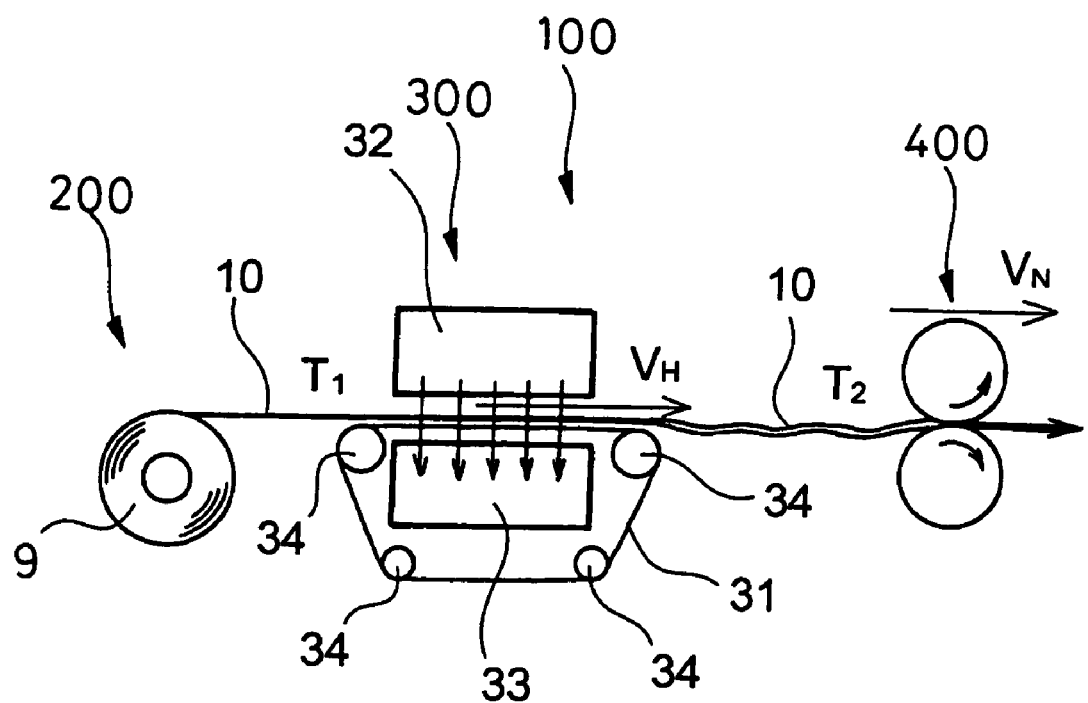
FIG. 5 schematically illustrates another apparatus which can be used to carry out a method of the present invention.

FIG. 5 schematically illustrates a bulkiness restoring apparatus which can be used to carry out another embodiment of the present invention. In FIG. 5, a nonwoven fabric 10 runs from the left hand side (upstream) toward the right hand side (downstream). The bulkiness restoring apparatus 100 shown in FIG. 5 comprises an unwinding unit 200, a hot air blowing unit 300 placed in the downstream of the unwinding unit 200, and a pair of nip rolls 400 placed in the downstream of the hot air blowing unit 300.

The unwinding unit 200 unwinds the nonwoven fabric 10 from a stock roll 9 at a given speed. The hot air blowing unit 300 has an air permeable conveyer belt 31 made of a wire mesh or resin, a blower 32, and a suction box 33. The conveyer belt 31, which is endless, runs in a direction around supporting axes 34. The conveyer belt 31 is formed of a metal or a resin, e.g., polyethylene terephthalate. A belt made of a resin such as polyethylene terephthalate is preferred from the standpoint of heat dissipation efficiency.

The blower 32 is placed above the conveyer belt 31 to face the upper run of the conveyer belt 31. The blower 32 blows hot air heated at a prescribed temperature toward the conveyer belt 31. On the opposite side of the upper run of the conveyer belt 31 is placed the suction box 33 which sucks the hot air blown from the blower 31. The hot air sucked by the suction box 33 is sent to the blower 32 through a duct (not shown). That is, hot air is circulated between the blower 32 and the suction box 33.

The nonwoven fabric 10 unwound from the stock roll 9 is led onto the conveyer belt 31 and carried into the hot air blowing unit 300, where hot air heated to a prescribed temperature is blown from the blower 32 to the conveyer belt 31. The nonwoven fabric 10 is thus heated by the hot air in the hot air blowing unit 300. The present inventors have unexpectedly found that the heat treatment by hot air blowing combined with the subsequent transfer at a negative draw ratio makes the nonwoven fabric 10 with reduced bulkiness increase its bulkiness to restore to substantially the same bulkiness as before. It has been ascertained in particular that the restoration is enhanced where hot air is blown through the nonwoven fabric 10 by a through-air technique. To adopt a through-air technique is additionally advantageous for reducing the hot air blowing time as described later.

Another advantage of adopting a through-air technique is that the nonwoven fabric 10 can be transferred stably and that changes in width that may be caused by heating is minimized. This is because the nonwoven fabric 10 is transferred while being pressed onto the conveyer belt 31 by hot air blown thereto.

The nonwoven fabric 10 coming out of the hot air blowing unit 300 is pinched between a pair of nip rolls 400 and transferred downstream. In this zone, the transfer speed is set lower than that in the heating zone of the hot air blowing unit 300 as long as the nonwoven fabric 10 is transferred stably. This operation, which is referred to as "transfer at a negative draw ratio", brings about ensured bulkiness restoration for the following reasons. Although not wanting to be limited by theory, the present inventors have found that reduction in bulkiness of nonwoven fabric in a roll form is mainly caused by two factors. One is the compression of nonwoven fabric in thickness direction, and the other is stretch of the nonwoven fabric due to winding tension. It has been ascertained that the reduction in bulkiness by the former cause is restored by the aforementioned heating and that the reduction in bulkiness by the latter cause is restored by allowing the heated nonwoven fabric to shrink while being transferred at a negative draw ratio. Through these two mechanisms of bulkiness restoration, the nonwoven fabric significantly restores its bulkiness.

The transfer at a negative draw ratio can be carried out as follows. In the hot air blowing unit 300, hot air is blown toward the nonwoven fabric 10 to press it to the conveyer belt 31. Accordingly, the nonwoven fabric 10 runs at substantially the same speed as the revolution velocity $V_H$ of the conveyer belt 31 without slip. As is generally practiced in the art in order to transfer sheeting of continuous length in a stable manner, the speed of the unwinding unit 200 for feeding the nonwoven fabric 10 is set slightly lower than the running speed of the nonwoven fabric 10 in the hot air blowing unit 300 so that an appropriate tension $T_1$ may be imposed to the nonwoven fabric 10 between the unwinding unit 200 and the hot air blowing unit 300.

Between the nip rolls 400, the nonwoven fabric 10 runs at the rotation velocity $V_N$ of the nip rolls 400. According to the above-mentioned common knowledge for stably transferring sheeting of continuous length, it would be common to set $V_N$ slightly higher than $V_H$ so as to give the nonwoven fabric 10 between the hot air blowing unit 300 and the nip rolls 400 a tension $T_2$ that is equal to or slightly higher than $T_1$. In this embodiment, in contrast, the nonwoven fabric 10 is transferred under conditions satisfying the relationship $V_H > V_N$. In other words, the heated nonwoven fabric 10 is transferred under a tension lower than that applied while heating. It suffices that the heated nonwoven fabric is transferred under a tension lower than that imposed to the nonwoven fabric while being heated (i.e., under a condition satisfying $T_1 > T_2$) as long as it moves stably. It does not matter whether such transfer conditions are achieved intentionally or unintentionally.

Where sheeting in continuous form is transferred as pinched between the nip rolls 400, it is a generally followed practice in the art to apply a sufficient nip pressure for giving an adequate tension to the sheeting. In this case, the sheeting often has its thickness reduced by compression under the nip pressure. In the present embodiment in contrast, since the nonwoven fabric 10 is transferred at a negative draw ratio, it is possible to reduce the nip pressure imposed to the nonwoven fabric 10 to such a degree as to give no excessive compressive force. Therefore, it occurs less that the bulkiness once restored by the heat treatment and the transfer at a negative draw ratio may be reduced again by the nip pressure.

In order to prevent the nonwoven fabric 10 from sagging and being transferred unstably while allowing the fabric 10 to sufficiently shrink to increase its bulkiness, the ratio of $V_H$ to $V_N$ is preferably greater than about 1 and is more preferably from about 1.005 to 1.5, even more preferably from about 1.01 to 1.1.

The bulkiness increase by transfer at a negative draw ratio takes place while the nonwoven fabric 10 is delivered from the hot air blowing unit 300 to the nip between the nip rolls 400. While depending on the kind, the basis weight, etc. of the nonwoven fabric 10, if the time for the nonwoven fabric 10 from coming out of the hot air blowing unit 300 to reaching the nip is extremely short, the nonwoven fabric can fail to sufficiently increase its bulkiness. From this viewpoint, the time from the nonwoven fabric 10's coming out of the hot air blowing unit 300 to reaching the nip rolls 400 is preferably about 0.5 second or longer, more preferably about 2 seconds or longer. The upper limit of this time period is preferably, while not particularly limited to, about 10 seconds, more preferably about 5 seconds, considering that an excessively long time does not result in an appreciable further increase in bulkiness and that unstable transfer caused by negative draw should be prevented. It is desirable for the nonwoven fabric 10 to be cooled at an ambient temperature to 50° C. or lower while being delivered from the hot air blowing unit 300 to the nip rolls 400.

Through the above-described operations, the nonwoven fabric 10 having had its bulkiness reduced by winding pressure restores bulkiness as before. The nonwoven fabric 10 with restored bulkiness is then subjected to any subsequent step of fabrication. The nonwoven fabric 10 is preferably sent to the subsequent step as is, i.e., without being wound into a roll. Various fabrication steps can follow according to the use of the nonwoven fabric 10.

Modification of the embodiment shown in FIG. 5 will now be described by way of FIG. 6 with reference to differences from the embodiment shown in FIG. 5. The explanation of the embodiment shown in FIG. 5 applies appropriately to those particulars of this embodiment that are not described here. The elements common to FIG. 5 are given the same reference numerals.

Figure 6:
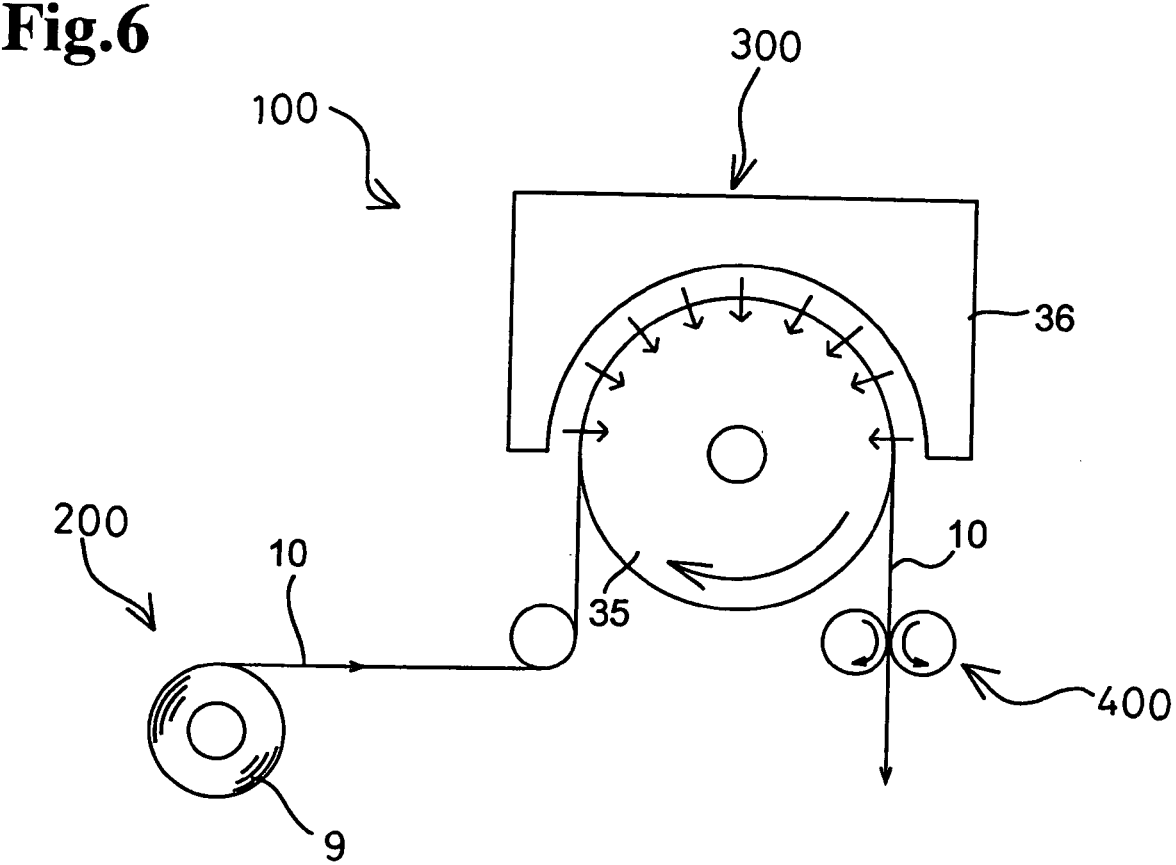
FIG. 6 schematically shows yet another apparatus which can be used to carry out a method of the present invention.

The apparatus 100 shown in FIG. 6 has a drum 35 in the hot air blowing unit 300. The nonwoven fabric 10 runs as wrapped on the drum 35. The peripheral surface of the drum 35 is made of an air permeable material, such as punching metal or wire mesh. The drum 35 is covered with a hood 36. Hot air is blown from inside the hood 36 toward the drum 35 and sucked into the drum 35. That is, hot air is blown through the nonwoven fabric 10 according to a through-air technique. The apparatus 100 of this embodiment is advantageous over that of the embodiment shown in FIG. 5 in terms of size reduction.

In the embodiments shown in FIGS. 5 and 6, the manner of heating the nonwoven fabric 10 is not limited to hot air blowing. The heating may be carried out by bringing the nonwoven fabric 10 into contact with a heated roll with a wrap or by means of an electric heater.

In the present invention, the embodiments shown in FIGS. 1 to 6 may be combined appropriately within the scope of the present invention.

EXAMPLES

The present invention will now be illustrated in greater detail with reference to Examples. The following Examples are presented as being exemplary of the present invention and should not be considered as limiting. Before describing Examples and Comparative Examples, the production of nonwoven fabrics will be described. Unless otherwise noted, all the parts and percents are by weight.

Preparation of Nonwoven Fabric A:

1) Preparation of First Layer

Thermoplastic conjugate fiber (ESC available from Chisso Corp.; sheath/core conjugate fiber with a three-dimensional crimp, composed of a polypropylene core and a polyethylene sheath; fineness: 3.3 dtex; fiber length: 51 mm; melting point of sheath: 131±2° C. (by DSC)) was carded into a web having a basis weight of 10 g/m², which was used as a first layer.

2) Preparation of Second Layer

A mixture of 70% of thermoplastic conjugate fiber (HR, from Ube-Nitto Kasei Co., Ltd.; sheath/core conjugate fiber with a two-dimensional crimp, composed of a polypropylene core and a polyethylene sheath; fineness: 2.2 dtex; fiber length: 51 mm; melting point of sheath: 130±2° C. (by DSC)) and 30% of thermoplastic conjugated fiber (ESC, from Chisso Corp.) was carded into a web having a basis weight of 15 g/m², which was used as a second layer.

3) Preparation of Nonwoven Fabric

The first and second layers were superposed on each other and united together by a through-air method to obtain a nonwoven fabric having a basis weight of 25 g/m². The resulting nonwoven fabric, designated A, was wound into a stock roll.

Preparation of Nonwoven Fabric B:

1) Preparation of First Layer

Thermoplastic conjugate fiber (SH available from Daiwabo Co., Ltd.; sheath/core conjugate fiber with a two-dimensional crimp, composed of a polyethylene terephthalate core and a polyethylene sheath; fineness: 2.2 dtex; fiber length: 51 mm; melting point of sheath: 132±2° C. (by DSC)) was carded into a web having a basis weight of 12 g/m², which was used as a first layer.

2) Preparation of Second Layer

Helically self-crimping fiber (CPP, from Daiwabo Co., Ltd.; composed of a polypropylene core and an ethylene-propylene random copolymer sheath; fineness: 2.2 dtex; fiber length: 51 mm) was carded into a web having a basis weight of 17 g/m², which was used as a second layer. The sheath material of the conjugate fiber CPP showed no clear peak in DSC analysis.

3) Preparation of Nonwoven Fabric

The first and the second layers were superposed on each other and partly joined together by heat embossing. The formed joints each had a circular shape and made, as a whole, a diamond lattice pattern as shown in FIG. 2(a). Hot air at 130±10° C. was blown to the joined layers from the top and bottom sides thereof for about 12 seconds using a pin-tenter equipped with a heat-shrinkage means. As a result, the self-crimping fiber of the second layer crimped in a helical configuration, and the second layer shrank, whereupon the parts of the first layer surrounded by the joints protruded. There was thus obtained a nonwoven fabric with a great number of protrusions on the first layer side as illustrated in FIG. 2(b) and having a basis weight of 58 g/m². The inside of the individual protrusions was found filled with fibers as depicted in FIG. 2(b). The resulting nonwoven fabric, designated B, was wound into a stock roll.

The results are shown in Table 1. The basis weights of the nonwoven fabrics A and B were 23 g/m² and 42 g/m², respectively, at the time of unwinding. Examples 1 to 5 and Comparative Examples 1 to 2 were carried out using the apparatus of FIG. 4 (with no cooling zone C). In Examples 6 and 7, hot air was blown to the nonwoven fabric in a tabletop hot air rapid drying oven and penetrated therethrough. In Comparative Examples 3 and 4, hot air from a hair dryer was blown to the nonwoven fabric but not penetrated therethrough. In Examples 1–7 and Comparative Example 3 and 4, the heated nonwoven fabric was allowed to cool spontaneously.

Method of Measuring Thickness of Nonwoven Fabric

The thickness of the nonwoven fabric before the hot air blowing was measured after 1 minute to 1 hour from the unwinding. The thickness of the nonwoven fabric after the hot air blowing was measured after 1 minute to 1 hour from the start of the hot air blowing. The measurements were made according to the method described below. The results obtained are shown in Table 1.

A 100 mm-side square was cut out of the nonwoven fabric to prepare a test piece. A plate smaller than the test piece (56.4 mm in diameter) and weighting 12.5 g was placed on a stage. The position of the upper plane of the plate was taken as a reference position A. Then the plate was removed, the test piece was put on the stage, and the plate was placed on the test piece. The position of the upper plane of the plate on the test piece was taken as B. The difference between A and B was obtained as a thickness of the nonwoven fabric under a load of 0.5 cN/cm². The measurements were made with a laser displacement meter (CCD laser displacement sensor LK-080, from Keyence), or otherwise with a dial thickness gauge. In using a dial thickness gauge, however, both the measuring load of the equipment and the weight of the plate should be adjusted to give a load of 0.5 cN/cm² to the test piece.

TABLE 1

| Example No. | Nonwoven Fabric | Transfer Speed (m/min) | Hot Air Temp. (° C.) | Blowing Time(sec) | Hot Air Velocity (m/sec) | Thickness (mm) Before Blowing | Thickness (mm) After Blowing |
|---|---|---|---|---|---|---|---|
| Example 1 | A | 25 | 130 | 1.13 | 6.1 | 0.50 | 1.53 |
| Example 2 | A | 100 | 110 | 0.28 | 4.0 | 0.50 | 1.74 |
| Example 3 | B | 100 | 110 | 0.28 | 3.4 | 1.06 | 2.41 |
| Example 4 | B | 25 | 130 | 1.13 | 3.4 | 1.06 | 2.38 |
| Example 5 | B | 180 | 90 | 0.16 | 3.4 | 1.06 | 1.99 |
| Example 6 | A | — | 120 | 3.00 | 1.07 | 0.51 | 1.66 |
| Example 7 | A | — | 110 | 1.00 | 0.81 | 0.51 | 0.99 |
| Comp. Ex. 1 | A | 150 | 70 | 0.19 | 6.1 | 0.50 | 0.77 |
| Comp. Ex. 2 | B | 100 | 70 | 0.28 | 4.0 | 1.06 | 1.67 |
| Comp. Ex. 3 | A | — | 120 | 3.00 | 22 | 0.38 | 0.46 |
| Comp. Ex. 4 | B | — | 120 | 3.00 | 22 | 0.83 | 0.98 |

Examples 1 to 7 and Comparative Examples 1 to 4

After the stock rolls of the nonwoven fabrics A and B were stored at room temperature (23° C.) for at least 2 months, each of the nonwoven fabrics A and B was unwound at the speed shown in Table 1 below, and hot air was blown thereto under the conditions shown in Table 1. The thicknesses of the respective nonwoven fabrics before and after the hot air blowing were measured by the following manner.

As is apparent from the results in Table 1, it is seen that the nonwoven fabrics treated by the method of the present invention restored the thickness to a great extent, whereas those treated by the comparative method showed only small thickness restoration.

According to the embodiments of the present invention, the bulkiness of nonwoven fabric that has been reduced by winding into a roll can easily be restored.

Furthermore, the bulkiness of nonwoven fabric can be restored efficiently with a small-sized apparatus.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application Nos. 2002-280081 filed Sep. 25, 2002 and 2003-180240 filed Jun. 24, 2003, which are incorporated herein by reference.

What is claimed is:

1. A method for restoring bulkiness of nonwoven fabric which contains crimped thermoplastic fiber and is in a roll form, which comprises:
   unwinding the nonwoven fabric in a roll form and
   blowing hot air to the unwound nonwoven fabric for from about 0.05 to 3 seconds, by a through-air technique, thereby increasing the bulkiness of the nonwoven fabric, wherein
   the hot air has a temperature lower than the melting point of the thermoplastic fiber and not lower than a temperature lower than the melting point by about 50° C.,
   the nonwoven fabric has a multilayer structure composed of at least two layers and contains the crimped thermoplastic fiber in an outermost layer thereof, and
   the nonwoven fabric contains heat shrinkable fiber in a layer other than the outermost layer containing the crimped thermoplastic fiber.

2. A method for restoring bulkiness of nonwoven fabric which contains crimped thermoplastic fiber and is in a roll form, which comprises:
   unwinding the nonwoven fabric in a roll form;
   blowing hot air to the unwound nonwoven fabric for from about 0.05 to 3 seconds, by a through-air technique, thereby increasing the bulkiness of the nonwoven fabric, wherein the hot air has a temperature lower than the melting point of the thermoplastic fiber and not lower than a temperature lower than the melting point by about 50° C.; and
   cooling the hot air-heated nonwoven fabric by blowing cool air to the nonwoven fabric by a through-air technique immediately after the hot air blowing, the temperature of the cool air being 50° C. or lower, the velocity of the cool air being from about 1 to 10 m/sec and the blowing time being about 0.01 second or longer, or
   by spontaneous cooling after the hot air blowing,
   wherein the nonwoven fabric is suppressed from shrinking in the width direction thereof so that the width of the nonwoven fabric after the cool air blowing is about 95% or more of the width of the nonwoven fabric before the hot air blowing.

3. The method according to claim 1 or 2, wherein the nonwoven fabric is produced by a through-air method.

4. The method according to claim 1 or 2, wherein the crimped thermoplastic fiber has a fineness of from about 1.1 to 11 dtex.

5. A process of producing a nonwoven fabric comprising:
   preparing a nonwoven fabric containing crimped thermoplastic fiber by a prescribed process and winding the nonwoven fabric into a stock roll,
   unwinding the nonwoven fabric from the stock roll, and
   blowing hot air for from about 0.05 to 3 seconds to the unwound nonwoven fabric by a through-air technique thereby increasing the bulkiness of the nonwoven fabric, wherein the hot air has a temperature lower than the melting point of the thermoplastic fiber and not lower than a temperature lower than that melting point by about 50° C., wherein
   the nonwoven fabric has a multilayer structure composed of at least two layers and contains the crimped thermoplastic fiber in an outermost layer thereof, and
   the nonwoven fabric contains heat shrinkable fiber in a layer other than the outermost layer containing the crimped thermoplastic fiber.

6. A process of producing an absorbent article comprising a liquid permeable topsheet, a liquid impermeable backsheet, and a liquid retentive absorbent member interposed between the topsheet and the backsheet,
   the topsheet being made of nonwoven fabric which contains crimped thermoplastic fiber and has been wound into a stock roll before being fabricated into the absorbent article,
   which process includes the steps of:
   unwinding the nonwoven fabric from the stock roll and
   blowing hot air for from about 0.05 to 3 seconds to the unwound nonwoven fabric by a through-air technique thereby increasing the bulkiness of the nonwoven fabric, wherein
   the hot air has a temperature lower than the melting point of the thermoplastic fiber and not lower than a temperature lower than that melting point by about 50° C.,
   the nonwoven fabric has a multilayer structure composed of at least two layers and contains the crimped thermoplastic fiber in an outermost layer thereof, and
   the nonwoven fabric contains heat shrinkable fiber in a layer other than the outermost layer containing the crimped thermoplastic fiber.

7. A process of producing an absorbent article comprising a liquid permeable topsheet, a liquid impermeable backsheet, a liquid retentive absorbent member interposed between the topsheet and the backsheet, and an intermediate sheet interposed between the topsheet and the absorbent member,
   at least one of the topsheet and the intermediate sheet being made of a nonwoven fabric which contains crimped thermoplastic fiber and has been wound into a stock roll before being fabricated into the absorbent article,
   which process includes the steps of:
   unwinding the nonwoven fabric from the stock roll and
   blowing hot air for from about 0.05 to 3 seconds to the unwound nonwoven fabric by a through-air technique thereby increasing the bulkiness of the nonwoven fabric, wherein
   the hot air has a temperature lower than the melting point of the thermoplastic fiber and not lower than a temperature lower than that melting point by about 50° C.,
   the nonwoven fabric has a multilayer structure composed of at least two layers and contains the crimped thermoplastic fiber in an outermost layer thereof, and
   the nonwoven fabric contains heat shrinkable fiber in a layer other than the outermost layer containing the crimped thermoplastic fiber.

8. A process of producing an absorbent article comprising a liquid permeable topsheet, a liquid impermeable backsheet, and a liquid retentive absorbent member interposed between the topsheet and the backsheet,
   the topsheet being made of nonwoven fabric which contains crimped thermoplastic fiber and has been wound into a stock roll before being fabricated into the absorbent article, which process includes the steps of:

unwinding the nonwoven fabric from the stock roll;

blowing hot air for from about 0.05 to 3 seconds to the unwound nonwoven fabric by a through-air technique thereby increasing the bulkiness of the nonwoven fabric, wherein the hot air has a temperature lower than the melting point of the thermoplastic fiber and not lower than a temperature lower than that melting point by about 50° C., and cooling the hot air-heated nonwoven fabric by blowing cool air to the nonwoven fabric by a through-air technique immediately after the hot air blowing, the temperature of the cool air being about 50° C., or lower, the velocity of the cool air being from about 1 to 10 m/sec and the blowing time being from about 0.01 second or longer, or by spontaneous cooling after the hot air blowing; and then packaging the absorbent article after cooling, wherein the nonwoven fabric is suppressed from shrinking in the width direction thereof so that the width of the nonwoven fabric after the cool air blowing is about 95% or more of the width of the nonwoven fabric before the hot air blowing.

9. The process of producing an absorbent article according to claim 6, which further includes the step of:

cooling the hot air-heated nonwoven fabric by blowing cool air to the nonwoven fabric by a through-air technique immediately after the hot air blowing, the temperature of the cool air being about 50° C., or lower, the velocity of the cool air being from about 1 to 10 m/sec and the blowing time being from about 0.01 second or longer, or by spontaneous cooling after the hot air blowing, and then packaging the absorbent article after cooling.

10. A method for restoring bulkiness of nonwoven fabric which contains crimped thermoplastic fiber and is in a roll form while the nonwoven fabric is unwound and transferred, the method comprising:

heating the unwound nonwoven fabric while the nonwoven fabric is being transferred at a heating temperature lower than the melting point of the thermoplastic fiber and not lower than a temperature lower than the melting point by about 50° C.; and transferring the heated nonwoven fabric at a speed lower than the transfer speed during the heating thereby to make the nonwoven fabric increase in bulkiness, wherein the heated nonwoven fabric is transferred under a tension lower than the tension imposed to the nonwoven fabric being heated.

11. The method according to claim 10, wherein the heating is carried out by blowing hot air heated to the heating temperature of the nonwoven fabric or bringing the nonwoven fabric into contact with a roll heated to the heating temperature with a wrap.

12. The method according to claim 11, wherein the heating is carried out by blowing hot air heated to the heating temperature to the nonwoven fabric by a through-air technique.

13. A method for restoring bulkiness of nonwoven fabric which contains crimped thermoplastic fiber and is in a roll form while the nonwoven fabric is unwound and transferred, the method comprising:

heating the unwound nonwoven fabric while the nonwoven fabric is being transferred at a heating temperature lower than the melting point of the thermoplastic fiber and not lower than a temperature lower than the melting point by about 50° C., and transferring the heated nonwoven fabric at a speed lower than the transfer speed during the heating thereby to make the nonwoven fabric increase in bulkiness, wherein the heating is carried out by blowing hot air heated to the heating temperature of the nonwoven fabric or bringing the nonwoven fabric into contact with a roll heated to the heating temperature with a wrap, the heating and the transferring are carried out by using a bulkiness restoring apparatus comprising an unwinding unit for unwinding the nonwoven fabric from a stock roll, a hot air blowing unit placed downstream of the unwinding unit, and a pair of nip rolls placed downstream of the hot air blowing unit, and the rotation speed of the nip rolls being lower than the nonwoven fabric transfer speed in the hot air blowing unit.

14. The method according to claim 11, wherein the hot air is blown for from about 0.05 to 3 seconds.

15. The method according to claim 10, wherein the nonwoven fabric has a multilayer structure composed of at least two layers and contains the crimped thermoplastic fiber in an outermost layer thereof, and the nonwoven fabric is heated from the outermost layer side thereof.

16. A process of producing an absorbent article comprising a liquid permeable topsheet, a liquid impermeable backsheet, and a liquid retentive absorbent member interposed between the topsheet and the backsheet, the topsheet being made of a nonwoven fabric which contains crimped thermoplastic fiber and has been wound into a stock roll before being fabricated into the absorbent article, which process includes the steps of:

unwinding and transferring the nonwoven fabric from a stock roll, heating the unwound nonwoven fabric while the nonwoven fabric is being transferred at a temperature lower than the melting point of the thermoplastic fiber and not lower than a temperature lower than that melting point by about 50° C., and transferring the heated nonwoven fabric at a speed lower than the transfer speed during the heating thereby to make the nonwoven fabric increase in bulkiness.

17. A method for restoring bulkiness of nonwoven fabric which contains crimped thermoplastic fiber and is in a roll form, which comprises:

unwinding the nonwoven fabric in a roll form and blowing hot air to the unwound nonwoven fabric for from about 0.05 to 3 seconds, by a through-air technique, thereby increasing the bulkiness of the nonwoven fabric without melting fibers constituting said nonwoven fabric, wherein the hot air has a temperature lower than the melting point of the thermoplastic fiber and not lower than a temperature lower than the melting point by about 50° C.

* * * * *